(12) United States Patent
Fuhr et al.

(10) Patent No.: US 7,393,629 B2
(45) Date of Patent: *Jul. 1, 2008

(54) METHOD AND DEVICES FOR TRANSFERRING BIOLOGICAL CELLS BETWEEN A CARRIER AND A PROBE

(75) Inventors: Günter R. Fuhr, Berlin (DE); Heiko Zimmermann, Kronberg (DE); Hagen Thielecke, Blieskastel (DE)

(73) Assignee: Fraunhofer-Gesellschaft zur Forderung der Angewandten Forschung e.V., Munich (DE)

( * ) Notice: Subject to any disclaimer, the term of this patent is extended or adjusted under 35 U.S.C. 154(b) by 213 days.

This patent is subject to a terminal disclaimer.

(21) Appl. No.: 10/545,829

(22) PCT Filed: Dec. 2, 2003

(86) PCT No.: PCT/EP03/13581

§ 371 (c)(1),
(2), (4) Date: Aug. 17, 2005

(87) PCT Pub. No.: WO2004/074424

PCT Pub. Date: Sep. 2, 2004

(65) Prior Publication Data

US 2006/0051735 A1    Mar. 9, 2006

(30) Foreign Application Priority Data

Feb. 21, 2003  (DE) .............................. 103 07 487

(51) Int. Cl.
*C12Q 1/00* (2006.01)
*C12N 5/00* (2006.01)

(52) U.S. Cl. .......................................... 435/4; 435/325

(58) Field of Classification Search ................. 435/325, 435/4
See application file for complete search history.

(56) References Cited

U.S. PATENT DOCUMENTS 5,877,008 A   3/1999   Remenyik et al.
6,517,779 B1  2/2003   Luttermann et al.

FOREIGN PATENT DOCUMENTS

| CH | 652 933 A5 | 12/1985 |
|---|---|---|
| DE | 197 14 987 C1 | 9/1998 |
| DE | 199 33 838 A1 | 2/2001 |
| EP | 0 539 888 A1 | 5/1993 |
| WO | 03/047738 A2 | 6/2003 |

OTHER PUBLICATIONS

U.S. Appl. No. 10/545,973.*
U.S. Appl. No. 10/546,023.*
Abercrombie et al., "The Locomotion of Fibroblasts in Culture", Experimental Cell Research 67, pp. 359-367 (1971).
Cramer, "Organization and polarity of actin filament networks in cells: implications for the mechanism of myosin-based cell motility", Biochem. Soc. Symp. 65, pp. 173-205 (1999).
Fuhr et al., "Cell Traces—Footprints of Individual Cells during Locomotion and Adhesion", Biol. Chem., vol. 379, pp. 1161-1173 (1998).
Alberts et al., "Molecular Biology of the Cell", pp. 972-978 (2002).
Nobuaki, Abstract of JP 2000-098258 (2000).

* cited by examiner

*Primary Examiner*—Ruth A Davis
(74) *Attorney, Agent, or Firm*—Caesar, Rivise, Bernstein, Cohen & Pokotilow, Ltd.

(57) ABSTRACT

A cell transfer method is described, in which transfer of at least one biological cell (21) describing a natural cell locomotion between a carrier (80) and a probe (10) is provided, and whereby positioning the probe (10) and the carrier (80) relative to one another in a transfer arrangement is provided, in which transfer of the cell (21) takes place due to the natural cell locomotion. Probes and cell manipulators for transferring biological cells are also described.

19 Claims, 5 Drawing Sheets

METHOD AND DEVICES FOR TRANSFERRING BIOLOGICAL CELLS BETWEEN A CARRIER AND A PROBE

BACKGROUND OF THE INVENTION

The present invention relates to methods for moving biological cells, in particular for transfer of at least one biological cell carrying out a natural cell locomotion between a carrier and a probe, such as e.g. cell transfer method for removing or for introducing biological cells or cell groups into or out of cell material, manipulation and/or examination devices, which are adapted for carrying out such methods, in particular probes for transfer of at least one biological cell from or to a carrier, cell manipulators, which have at least one such manipulation and/or examination device, and applications of the abovementioned methods.

In medicine, biotechnology and biochemistry there are countless methods in which biological cells are examined or processed or used for examination or processing (modifying) biological material. For example cells are removed for medical cell therapy from an animal or human proband, treated, collected, sorted and/or cultivated outside the proband body in order to then recycle specific cells or cell groups in the probands. Specific advantages are expected from medical cell therapy with stem cells, since they possess the ability of differentiating almost all cell types of the body and therefore represent candidates for individual cell therapies and for in-vitro regeneration of tissue. Today it is assumed that under appropriate conditions adult or embryonic stem cells are suited to virtually all cell output of the body and therefore also for developing or regenerating different tissues. There is therefore strong interest in secure and reproducible handling of biological cells.

Essential tasks with examination or manipulation of biological cells, in particular in connection with medical cell therapy and tissue engineering, comprise the fact that individual, previously selected cells or cell groups can be added or removed, or defined measurements can be taken at predetermined locations, for example in the tissue or in a cell bond with precision in the μm range. To date e.g. stem cells are transmitted into target tissue using a syringe. These tasks must be solvable without impairment or damage to the cells or the tissues, and with a high degree of reproducibility, controllability and precision. These requirements however have not been satisfactorily answered to date.

It is known from practice that contradictory results have been achieved in animal testing despite similarly carried out methods, e.g. by injection of cells into diseased tissue. It was found that the positive course of tissue regeneration depends sensitively on the procedural conditions, in particular on the type of injection, the number of introduced cells or substances and the injection tool used. In numerous experiments it was not the desired regeneration or new development of a cell or tissue type which occurred, but for example induction of tumours. It is assumed that the induction of tumours as uncontrolled cell increase of stem cells is promoted through physical, chemical or outside mechanical influences at the injection site. These influences cannot be adjusted or at least acquired reproducibly with conventional injection techniques.

Stress-free and selective removal of adherent growing cells from in vitro cultures causes the following problems. First, mechanical scraping of the desired cells is possible. But at the same time there is the abovementioned risk of damage. Alternatively, detachment can be provided by trypsination, which represents a strong, unphysiological biochemical intervention in the cell culture, with the result that the adhesion proteins of the detached cells must be newly expressed. Also, trypsination constitutes a problem for selectivity of the cell removal. Selected cells can be rediscovered after trypsination only and removed individually from the culture with difficulty.

These problems in the cell therapy and results from tissue engineering, to date partially unsatisfying, currently constitute the most significant limitations and delays with a wide application of these methods in biotechnology and medicine.

The object of the invention is to provide improved methods for movement of biological cells relative to a foreign body, such as for example a carrier and a probe, with which the disadvantages of conventional methods are overcome and which enable in particular a smooth cell transfer between the carrier and the probe, whereby mechanical or biochemical influences on the transferred cell or on cells, present if necessary on the carrier or the probe, are to be minimised. In particular unphysiological interventions, such as trypsination, should be avoided in the cell material. The object of the invention is also to provide improved manipulation and/or examination devices (probes) for performing such methods, and cell manipulators, which are equipped with at least one such probe, with which the disadvantages of conventional injection or biopsy instruments can be overcome. The object of the invention is also to provide novel applications of probes for transfer of cells.

SUMMARY OF THE INVENTION

With respect to method the invention is based on the general technical teaching of further developing a cell transfer method, wherein at least one biological cell, which has natural intrinsic motion and, on contact with solid surfaces, describes a cell locomotion on the latter, is transferred between a carrier and a probe, to the extent that the probe and the carrier are arranged adjacent to one another or contiguously such that at least one biological cell is moved by the natural cell locomotion from the carrier to the probe (or vice versa from the probe to the carrier). The mutual aligning of the carrier and the probe is designated as transfer arrangement. The inventors have found that the transfer can take place sufficiently quickly, surprisingly for practice, on the basis of high cell mobility (e.g. within 1 hour or less).

Natural cell locomotion is understood here in general as the changing of place of a complete cell on a solid surface or in cell material by rearrangement of adhesion contacts of cell organs (membrane organs, for example membrane protrusions), such as described for example by M. Abercrombie et al. in the publication "The Locomotion Of Fibroblasts In Culture" ("Experimental Cell Research", vol. 67, 1971, pp. 359-367) and by L. P. Cramer in the publication "Organization and polarity of actin filament networks in cells: implications for the mechanism of myosin-based cell motility" ("Biochem. Soc. Symp." vol. 65, 1999, pp. 173-205). In terms of the invention cell locomotion occurs directly from the surface of the probe to the surface of the carrier (or vice versa), without the cell at one time detaching from both surfaces. Cell material is understood here in general as a plurality of cells, which are in contact with their environment via adhesion contacts (macromolecular chemical compounds, no van der Waals bonds). The cell material is for example a bond or grouping together of individual cells, a cell culture, a tissue (bond of differentiated cells of the same kind) or an organ. The cell material, in particular the non-fluid composite of individual cells can contain additional synthetic components, for example a synthetic matrix material. The result therefore is advantageously a wide field of application of the invention.

The transferred cells preferably include animal or human cells, such as for example fibroblasts, macrophages, lymphocytes, tumour cells or nerve cells.

Particular advantages can come about if the inventive method is performed on cell material, which is located outside an animal or human organism. Under suitable cultivation conditions the cell material can be arranged on the carrier. The positioning of the cell material and the probe can be simplified and carried out with increased precision.

Alternatively, the cell material can be found as a compound in a living organism. The probe can for example be set on or inserted into tissue as an examination probe, a biopsy instrument or injection tool. The insertion takes place due to the minimal velocity of advance in the positioning or continuous relative movement (see below) in a state, in which the affected tissue is fixed, e.g. is held with the surrounding part of the organism immobile on a carrier. The use of an anaesthetic is preferred to keep the subject still, with a view to avoiding injury by the method, however is not absolutely required.

The probe and the carrier are generally separate foreign bodies or objects made of a material with a solid surface which can be delimited with respect to the cell or the cell material. The probe can in particular comprise a manipulation and/or examination device such as an injection capillary. The carrier can in particular comprise a culture support known per se, with individual cells or a cell culture, such as e.g. a glass or plastic dish.

The inventors have found that the natural cell locomotion and fluctuation in the macromolecular binding to surfaces can surprisingly be utilised so that the cell can be moved from one solid body (e.g. the carrier) to another, separate solid body (e.g. the probe). Advantageously it is possible merely by positioning the probe and the carrier in the transfer arrangement to take up one or more cells for example from the carrier, without the biochemical or mechanical conditions for cells remaining on the carrier, or for the moved cell, to be disturbed disadvantageously. Individual cells or cell groups can be taken up or set down injury-free with the probe. During the positioning of probe and carrier, the involved cells remain unchanged in their physical and chemical state. The injury-free transfer is made in particular whenever in the movement of the cell the former and if necessary surrounding cells of a cell culture are deformed and if necessary their spatial position is changed, however no chemical signals are given off in the form of messenger substances or substance separation.

The invention is also based on the following considerations by the inventors. First it was recognised that the reactions, to date occurring in different ways for example, with cells injected into a tissue or a cell bond are caused as cells are injured or destroyed in the available cell material by conventional introduction of a tool and therefore wound effects are induced. Wounds represent biochemically other boundary conditions, than would be the case in the undamaged tissue. With cell or tissue wounding chemical signals (the sending of molecular messenger substances) or cellular-supported processes, such as e.g. fibroblast immigration, fibronectin emigration or the like are generated. The reaction of damaged cells influences the effect of the injected cells or additives. For example, in the environment of cell wounding stem cells behave differently to stem cells in an intact cell material. Secondly, the inventors have found that contrary to evidence to date cells even bound adhesively to a substrate can migrate injury-free onto an adjacent substrate.

Due to the natural intrinsic motion of the cell the abovementioned requisites can be fully satisfied. Neither target tissue nor the individual cells to be inserted are damaged or impaired. The physical, chemical and mechanical state of the cells can be fully characterised. Damaging contact between cells and surfaces of foreign bodies is avoided, and cellular signals made by unwanted surface contact are prevented. Due to injury-free movement the cell manipulation takes place ideally smoothly. The probe can be guided with targeted precision to a predetermined site in the cell material on the carrier.

In accordance with a first preferred embodiment of the invention the cell transfer method is applied in the removal at least of one biological cell from the carrier. The probe forms a biopsy tool. Unphysiologically rapid, mechanical tearing off of adhesion contacts or their biochemical interruption by means of trypsination is advantageously avoided. When cell material is arranged on the carrier, from which the cell is taken and transferred to the probe, there is the additional advantage that this material also remains undisturbed and undamaged, with respect to its biochemical conditions. In this embodiment advantages for obtaining non-modified, physiological cells can result.

If, according to a modified variant of the invention, at least one sensor is arranged on or in the probe, it is advantageously possible that immediately after or before transfer at least one property of the cell, such as e.g. the membrane potential, the separation of substances, the impedance of the cell or fluorescence can be measured. It can be decided immediately whether the cell located on the probe satisfies predetermined selection criteria or not.

Examining the cell on the probe in particular has advantages for automating the inventive cell transfer method.

In general after the cell transfer it is preferably provided that the probe with the cell e.g. is moved to a target substrate. The advantage of removing the probe with the cell from the carrier is that further manipulation of the removed cell can be carried out independently of the handling of the carrier, in particular of further adjustment of culture conditions at the carrier. Removing the probe with the cell can be provided in particular dependent on measuring cell properties on the probe.

In contrast to the abovementioned first embodiment of the invention it can be provided according to an alternative variant that at least one biological cell is transferred from the probe to the carrier. Injury to the moving cell or from cell material to the carrier is also advantageously excluded in this case on account of the intrinsic motion of the cell. If according to a preferred application of the invention, cell material is arranged on the carrier, the probe can be positioned on the cell material contiguously or projecting into the latter, whereby damage to the cell material is avoided.

This alternative can offer particular advantages for intentional applications in biotechnology and medicine, since when the cell is embedded in the cell material it is present in a physiologically undamaged state. The at least one cell is embedded on or in the undamaged cell material. In particular, stem cells can be implanted in tissue to cause tissue-specific differentiation of the stem cells. Degeneration or development of tumours can be suppressed.

If according to a preferred embodiment of the invention the probe and the carrier make contact in the transfer arrangement, advantages can result from this with respect to the precision of the probe positioning and the speed of the cell transfer. The mutual contact of the probe and of the carrier can also advantageously be provided, in case a cell culture is arranged on the carrier. In this case cells of the cell culture are displaced without injuries by the probe in the positioning (see below). If, alternatively, the probe and the carrier, on which cell material is already arranged prior to transfer, are arranged at a distance for the cell transfer, which is substantially identical to or less than the extension of the cell material over the surface of the carrier, there can be advantages for precise setting or embedding of cells on or in the cell material.

In accordance with a further particularly preferred embodiment of the invention the relative position of the probe and of the carrier can be altered before and/or during the cell transfer. If the transfer arrangement between carrier and probe is altered, the selectivity and speed of the cell transfer can therefore be influenced advantageously.

The relative velocity of probe and carrier is preferably selected less than or equal to the speed of natural cell locomotion (1 µm/h to 1 mm/h).

If, with mutual alignment of probe and of carrier, it is provided that the probe firstly does not contact cell material on the carrier and then, after a specific cell is selected from the cell material, temporary contact is formed exclusively of the selected cell with the probe, the distance can be increased after forming contact, without contact between the selected cell and the probe being broken. The inventors have found that the cell organs can surprisingly maintain connections even over free spaces (e.g. 50 µm) and overcome such by the natural cell locomotion. With this variant only the selected cell is transferred, whereas the other cells remain on the carrier. This embodiment can be carried out vice versa, for example to transfer only one of several cells on the probe to the carrier.

In addition, a relative movement of probe and carrier can advantageously enable acceleration of the cell transfer. For example, during transfer from the carrier to the probe the latter is pushed under the cell opposite to the migration direction of the cell. And vice versa, during transfer to the carrier the probe can be drawn back opposite to the cell locomotion. At the same time the probe can project into the cell material on the carrier. The relative movement occurs such that the probe displaces the cells or the cell material injury-free or detaches from the cell or the cell material injury-free. The probe is actuated for example in the cell material such that the cells are pushed away from one another by the surface of the probe or are separated from one another, so that room is made for the probe, whereby the cells remain unchanged in their physical and chemical state during shifting or separation. Injury-free displacement of cells is in particular obtained when in the movement of the probe the cells are in direct contact with the probe body or cells lying more deeply in the cell material are deformed or change their spatial position, however they give off no chemical signals e.g. in the form of messenger substances or substance secretions.

This enables the mechanical introduction of the probe into cell material opposite to the direction of motion of a selected cell. The cells remaining on the carrier remain uninjured during movement of the probe through the cell material, if the velocity of advance is sufficiently low, so that the adhesion contacts between the cells are detached in a natural way, i.e. a way not influencing or destroying the cells, and can be rebuilt in the changing environment.

If a probe with a longitudinally extending form is used for the inventive cell transfer, it can be an advantage if the probe is moved relative to the carrier in a direction running parallel to the alignment of a longitudinally extending form of the probe. At the same time advantages can result with respect to the injury-free displacement of the cells. Displacement must take place only on the front side of the probe, which constitutes a very small surface section compared to the remaining surface. Also, the advantage of this embodiment is being compatible with conventional injection techniques using syringes, canulae or capillaries. The probe can be combined with devices available for manipulation of cells or cell suspensions. In particular, it is possible to fed a substance with the probe into the cell material. Fluid feed mechanisms, such as e.g. pumps or the like and known per se, can advantageously be used for this purpose.

In accordance with a preferred embodiment of the invention the probe is moved with a velocity of advance, which is less than or the same as a reference velocity, determined by the physiological binding rate of biological cells (locomotion or binding velocity of cells). With adjustment of this velocity of advance, the probe can be moved advantageously injury-free through cells in a naturally given composite. The velocity of advance is adapted to the permanent cell locomotion taking place in the tissue. It is for example known that specific types of immune cells (e.g. macrophages) are moved by displacement of present cells even through dense tissue. The inventors have established that surprisingly this displacement motion can also be brought about using probes, which are considerably larger than immune cells and have macroscopic dimensions in the sub-millimetre to centimetre range, during adjustment of said velocity of advance. During the probe movement macromolecular bonds (for example membrane-side macromolecules of the Integrin and Catherine family) are continuously separated between the cells and relinked for example with the probe surface.

The physiological reference velocity is known per se (see e.g. G. Fuhr et al. In "Biol. Chem.", 1998, vol. 379, pp. 1161-1173) or can be measured on animal or human cells. The interesting binding rate can be derived for example by measuring the dynamics of adhesion patterns of individual cells on synthetic surfaces.

Particular advantages of the invention result when the velocity of advance of the probe is selected in a speed range of 0.1 µm/h to 1 mm/h, preferably in the range of 1 µm/h to 500 µm/h. Corresponding to this speed range are the binding rates of the formation and decomposition of macromolecular bonds, which typically are mediated by membrane-side macromolecules of the Integrin and Catherine family. The preferred speed ranges correspond to the velocities of cell locomotion of in particular fibroplasts, macrophages, lymphocytes, chondrocytes or tumour cells. The position of the probe with a high degree of precision of up to +/−1 µm can advantageously be adjusted in setting such a minimal velocity of advance. The velocities of advances in said ranges correspond to the active endogenous locomotion speeds of cells in and on tissue. The movement of the probe therefore causes permanent building and rebuilding of the cells in the immediate environment of the probe surface, whereby displacement of the cells is promoted by the permanently working advance force.

Depending on application, different types of motion of the probe, in particular movements with a net advance or a net retreat, discontinuous movements or movements split into partial sections, oscillatory, uniform or accelerated movements can advantageously be made.

When the positioning and/or movement of carrier and probe relative to one another can be controlled depending on the outcome of an image recording and processing, advantages for a targeted rough positioning and/or counter movement of the probe relative to the natural cell locomotion can result, such that cell transfer can be accelerated. If for example the position of a selected cell to be transferred is first detected by microscopic observation, a start position for adjusting the transfer position can be commenced with a rapid movement. A movement detection comprises measuring natural cell locomotion. It advantageously enables the generation of control signals for a drive device of the carrier or the probe. In this case the automated removal of cells from a cell culture or the deposit of cells, for example with a control circuit, can be simplified.

A further advantage of the invention comprises the cell transfer being performed sequentially or in parallel with a plurality of cells. In particular, the following variants can be provided individually or in combination. First, following a first cell transfer from a carrier to the probe a further cell transfer can be provided from the probe to a further carrier, such as e.g. a target substrate or in an examination device. Secondly, several cells can successively migrate to a probe and jointly be removed by the carrier. Third, the probe can be configured such that several cells are transferred at the same time to the probe. In this case there can be advantages with respect to the speed of the cell manipulation.

With respect to equipment the abovementioned object is solved by a probe for cell transfer from or to a carrier, which has a probe body positionable relative to the carrier, on the end whereof facing the carrier a pick-up tool is provided, which has a carrying surface for adherent sticking of at least one biological cell. The advantage of the probe is that for performing the inventive cell transfer the pick-up tool as such is designed passively and needs no movable parts, such as e.g. microsurgical elements. The pick-up tool asconstitutes only one independent, miniaturisable cell carrier, to which or from which at least one cell migrates during cell transfer.

In accordance with a preferred embodiment of the invention the probe body can have a longitudinally extending, longitudinal form such as a bar or a rod, on the free end whereof the pick-up tool is arranged, whereby the probe body can be attached to a drive device with the opposite end. Advantageously, this configuration prevents obstacles to visibility with optical monitoring of cell material and cell transfer. Also, there can be advantages for advance motion of the probe in a direction parallel to the form of the probe body.

In accordance with a further preferred embodiment of the invention the pick-up tool is formed as part of the probe body. In this case the construction of the probe is particularly simple.

If the probe body according to a further modification has a cavity, extending e.g. along the longitudinal form, additional advantages for creating specific environmental conditions on the pick-up tool, such as e.g. providing an enveloping fluid, or for examining the cell on the probe can be obtained. To form a probe with a cavity it can for example be provided that the probe body has a longitudinally extending along a straight axis (capillary, tube, hollow needle, hose) with a first end, on which the pick-up tool is provided, and a second end, which can be connected to the drive device and if necessary to a reservoir device. This embodiment of the invention can have advantages because of its compatibility with conventional injection tools.

With a probe body with an inner space the pick-up tool can be arranged in the probe body (hollow body). The pick-up tool can be arranged to slide mobile in the hollow body, so that during cell transfer it protrudes on the free end of the hollow body and can be retracted into the hollow body after a cell is picked up.

The pick-up tool generally forms a carrying surface, which according to preferred embodiments of the invention has a concave or convex form. The concave form offers the advantage of spatial limiting of the carrying surface from the remaining probe body. This can prevent unwanted cell locomotion on the surface of the probe body. The concave pick-up tool is for example designed in the shape of a shovel or spoon. The convex form can be an advantage for injury-free movement of the probe through cell material. A convex pick-up tool with a spherical surface as a receptacle is preferably provided in a probe with the pick-up tool movable in the hollow body.

Alternatively, more complex formed pick-up tools can be provided, in case the pick-up tool is to be used to fulfil additional functions for example for measuring on the cell or for delimiting the cell from the surrounding cell material. The pick-up tool can be designed annular for example, whereby the carrying surface is provided on the inner side of the ring. An advantageous modification is offered with a dish-shaped or spherical pick-up tool, whereof the inside forms the carrying surface. If an opening is provided on the side of this pick-up tool facing the carrier, it can advantageously be set on a carrier or the cell material on the carrier and then withdrawn, as soon as at least one cell has moved on the inner surface of the dish or semi-circular form. Cell transfer is obtained after a short period with each direction of the natural cell locomotion by the annular form of the pick-up tool.

In accordance with a further variant of the invention it can be provided that the pick-up tool at the end of the probe body is fitted with at least one spacer, with which the pick-up tool can be set on the carrier. The spacer e.g. in the form of a protrusion, pin or web advantageously fulfils a double function. First, the precision of positioning the probe on the carrier can be increased. Second, the spacer serves as carrying surface for a cell to be picked up or set down. The spacer or spacers can dimensioned such that in each case only one cell reaches the cell-carrying surface. The selectivity of the cell transfer is thus increased.

In accordance with a further preferred embodiment of the invention the carrying surface of the pick-up tool has a material (binding material), which promotes adherent sticking of cells on the surface. The binding material forms the probe body, the pick-up tool, at least the front side (carrying surface) of the pick-up tool or a coating at least on the front side of the pick-up tool. It comprises for example fibronectin or collagen or surface wrinkling with typical dimensions in the nm to µm range. This embodiment of the invention can have advantages with respect to an increase in binding velocity during cell transfer.

The binding material can alternatively have surface wrinkling with characteristic structural sizes in the sub-µm range, so that binding of the cell material to the probe is promoted. The use of an adhesion-enhancing material constitutes an essential and fundamental difference of the inventive tool compared to conventional injection needles.

A further advantage of the invention comprises not limiting the probe to the use of rigid glass synthetic or metal materials, in contrast, for example, to conventional biopsy needles for sampling. The probe can rather comprise a flexible material, preferably an elastically deformable material deformable at least on the free end of the probe body and in particular on the pick-up tool. For example, the pick-up tool can comprise a flexible synthetic lamella, film or membrane (e.g. dialysis film, polyurethane), which is positioned for the inventive cell transfer on the carrier, until the at least one cell has been picked up.

For the abovementioned examination of the cell on or in the probe the latter is equipped preferably with at least one sensor. The at least one sensor can be set up to detect chemical or physical properties of cells or substances in the cell material or in the interior of the probe body. If at least one sensor, for example an impedance sensor is arranged in the cavity of the probe body, this will result in advantages for monitoring an injection or a biopsy.

The probe can also have at least one electrical conductor, which runs to the front side of the probe. The conductor can for example be melted in the probe and form a measuring electrode. At least a light guide for example for spectroscopic measuring in the cell material can also be provided.

According to the present invention the pick-up tool can have a rounded surface at least on its front side, which faces the carrier during cell transfer. In accordance with a preferred embodiment of the invention the front side of the probe has, in individual areas of the rounded surface, a local radius of curvature, which is greater than 10 µm. The rounded surface is thus greater than the cell types in the typically processed cell materials, in particular cell types in tissue. Therefore the probability of injury in the movement of the probe is reduced. Particular advantages can result with a local radius of curvature, which is greater than 20 µm, preferably greater than 0.1 mm. For application in cell cultures the radius of curvature is less than 5 mm, preferably less than 2 mm.

If according to a further modification the pick-up tool is transparent, this can facilitate optical viewing of the cell transfer.

A further subject of the invention is a cell manipulator (in particular a work unit such as for example an injection, biopsy and/or examination device) for processing cell material, whereby the cell manipulator comprises at least one inventive probe, a carrier for accommodating at least one cell or cell material, such as for example a cell culture and at least one drive device for adjusting a transfer arrangement of the probe or of the carrier. The cell manipulator has the particular advantage that the probe and the carrier with the drive device can be positioned relative to one another and if necessary can be moved with higher precision and reproducibility.

The drive device is preferably adapted for movement of the probe and/or of the carrier at a relative velocity, which is less than or equal to the abovementioned physiological reference velocity of the cell. This feature is of significance not only if the carrier and the cell are moved relative to one another during cell transfer, but also for adjusting the transfer position with a probe resting relative to the carrier. Injuries to the cell material on the carrier can advantageously be avoided also in positioning the probe and the carrier relative to one another.

If the drive device comprises a piezoelectric drive, then there are advantages for the precision and reproducibility of the probe movement. Alternatively, the drive device can be formed by a magnetic drive, leading to advantages with respect to contact-free transfer of the advance force. Furthermore, the drive device can comprise a spring-loaded drive, which can offer advantages with respect to particularly simple construction of the probe, or a thermal drive, in which an expansion or shrinkage movement of a probe material is utilised.

In accordance with preferred embodiments of the invention the cell manipulator is equipped with a positioning device for aligning the probe, the carrier and the drive device, and/or with a detector device for detecting the position or movement of the probe, the carrier or cells.

Preferred applications of the invention are in vitro cell culture, tissue engineering in biotechnology, provision of tissue models for pharmacology and medical therapy.

BRIEF DESCRIPTION OF SEVERAL VIEWS OF THE DRAWINGS

Further details and advantages of the invention are described hereinbelow with respect to the attached diagrams, in which.

DETAILED DESCRIPTION OF THE PREFERRED EMBODIMENTS

The invention is described hereinbelow with exemplary reference to embodiments, which illustrate the natural cell locomotion from the carrier to the probe and the function of the cell manipulator. The natural cell locomotion and the its characterisation and manipulation thereof are not explained, insofar as its details are known as such. For this purpose for example reference is made to the abovementioned publication by L. P. Cramer. It is emphasised also that if in the described embodiments reference is mostly made to cell transfer from the carrier to the probe, the invention can be implemented using the reverse direction of motion from the probe to the carrier accordingly.

Figure 1:
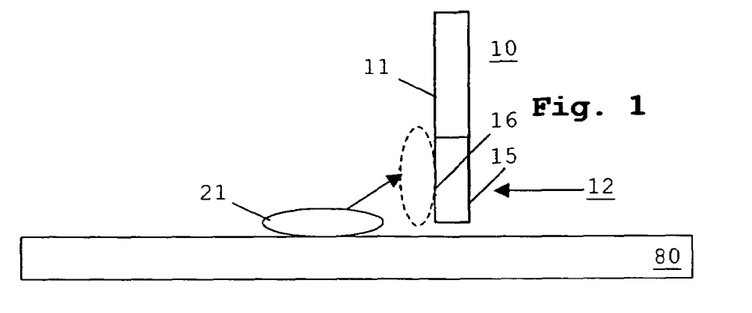
FIG. 1 is a schematic illustration of a combination of a probe and a carrier for carrying out an inventive cell transfer.

FIG. 1 shows schematically as basic components for carrying out the inventive cell transfer method a probe 10 and a carrier 80, which are arranged in a mutual transfer arrangement such that due to its natural cell locomotion a cell 21 can migrate from the surface of the carrier 80, e.g. out of a cell culture, onto the probe 10. The probe 10 comprises a probe body 11, at the free end 12 whereof the pick-up tool 15 is formed. The carrier 80 is for example a cell culture dish, on the bottom of which a cell culture is formed or a substrate in a cultivation system.

The locomotion of the cell 21 from the carrier 80 to the probe 10 takes place such that adhesion contacts of cell membrane organs are first detached from the carrier 80 and are formed again on the carrying surface 16 of the pick-up tool 15. During the course of cell locomotion adhesion contacts with the carrier 80 are increasingly separated, until the cell 21 is located fully on the pick-up tool 15. In general natural cell locomotion on an isotropic surface is undirected and stochastic. To implement the invention it can be sufficient if the cell migrates randomly on the probe within the scope of stochastic movement. Due to the high cell mobility under practical conditions a cell can be taken up onto the probe sufficiently rapidly in this case as well (e.g. within 1 to 2 hours). However, measures for directional cell migration on the probe or for enhancing transfer movement are preferably taken.

To avoid unwanted migration of the cell on the probe body coating or treatment for decrease of adhesion can be provided on and if necessary in the latter. For example, silanising or coating with biological macromolecules (for example Poly-Hema) is carried out.

Figure 2:
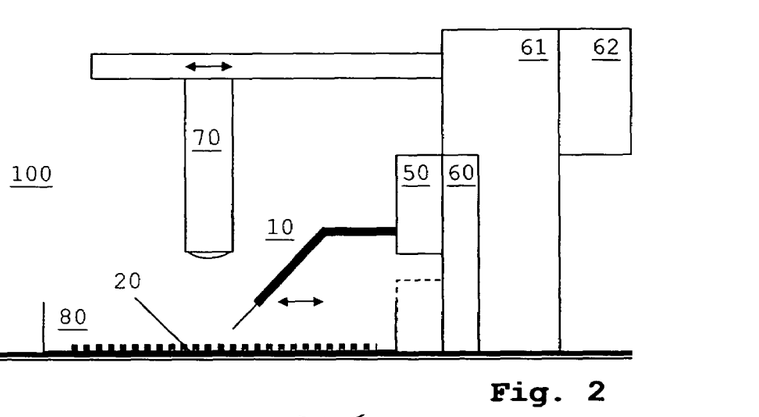
FIG. 2 is a schematic overview of an inventive cell manipulator.

An inventive cell manipulator 100 comprises, according to the schematic illustration in FIG. 2, the probe 10, the drive device 50, a positioning device 60, a detector device 70, the carrier 80 with a cell culture 20 and a fluid covering 81, and a control device 61. The fluid covering 81 comprises e.g. a suspension und culture fluid, which advantageously does not hinder the inventive cell transfer.

The purpose of the drive device 50 is to adjust the transfer arrangement of probe 10 and carrier 80 and if necessary to exert an advance force on the probe 10 during cell transfer. The drive device 50 contains e.g. piezocrystals, with which the probe 10 can be positioned and moved similarly to micromanipulator systems known per se in different spatial directions, with a precision of <100 nm. The work path of the probe 10 can be between 0.1 mm and a few centimetres. Alternatively, the drive device 50 (shown in dashed lines) can be set up for movement of the carrier 80 of the cell material.

The drive device 50 is connected to the positioning device 60. The positioning device 60 is a component which can be fixed mechanically stably and micrometer-precisely relative to the carrier 80. Its task is to guarantee the stable position of the probe relative to the carrier over the duration of manipulation (hours, days or even weeks). This can be achieved by an adjustable three-point mounting on the culture system (see FIG. 8) or anchoring e.g. on the bone of the skull in the case of a cell injection into the brain. The positioning device 60 is also set up for movements of the probe or the carrier over greater distances and at greater speeds, which are preferred before or after adjustment of the transfer arrangement of probe and carrier, and for this purpose contains a servomotor for example.

The positioning device 60 is also connected to the control device 61 and a measuring and display device 62. The control device 61 serves to control the overall system and contains a processor or computer. The current and planned positions will be monitored via sensors (strain gauges on actuators, 4-quadrant detection by means of laser beam as in atomic force microscopy or in similar fashion). The information is processed software-based and displayed such that the real and planned movement is represented on a monitor along with purposeful parameters. A camera system with microscopic enlargement and a zoom function can be provided as detector device 70 for this purpose.

The probe 10 can be connected to a sample reservoir (not shown), which contains a transport system for movement of a sample into the probe 10. The cell to be transferred to the cell material is contained for example in a cell suspension. The transport system is a feed mechanism known per se such as e.g. a precision injection pump. The sample reservoir for taking up the cells to be injected can be a Hamilton injector or a container connected via a 3-way system having low dead volume. Using mechanical compression the transport system presses for example a cell suspension into the injection tools (probe 10). Thereby, very minimal volumes are to be moved (speed a few μm/min). Rinsing procedures with washing solutions (speed 1 to a few 100 μm/s) can also be carried out. This can be achieved via programmable injection pumps.

Figure 3:
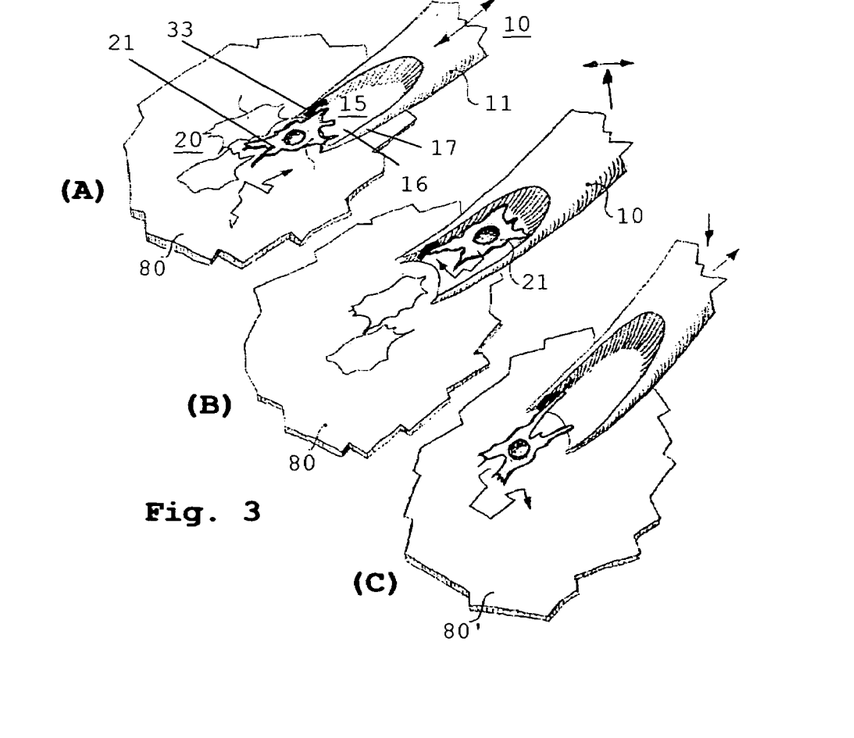
FIG. 3 shows the sequence of cell transfer steps according to an embodiment of the inventive method.

In accordance with FIG. 3 the pick-up tool 15 of the probe 10 is formed like a shovel on the end of a capillary-like probe body 11 with a hollow channel 31. The end of the probe body 11 is cut obliquely so that the pick-up tool 15 forms a slide or a shovel with a concave carrying surface 16 and edges 17 projecting therefrom. The probe 10 can be shifted with the drive and positioning devices 50, 60 (see FIG. 2) in all spatial directions and in particular along the longitudinal axis of the probe body 11 (see double arrow).

The probe body 11 comprises for example glass, an inert metal (e.g. platinum) or an inert synthetic material (e.g. polyimide). The inner diameter a of the hollow channel 31 at the opening 32 and the outer diameter b of the probe body 11 at its end are typically selected in the ranges a=10 μm to 100 μm and b=10.5 μm to 200 μm. Smaller measures in the range a=0.1 μm to 10 μm can be selected for transfer of particularly small cells or synthetic particles or greater measures of e.g. a=100 μm to 5 mm for transfer e.g. of embryonic stem cells, whereby the measure b corresponding to the wall thickness of the probe body 11 is accordingly greater.

The probe 10 can be provided with an impedance sensor 33. The impedance sensor 33 comprises two semicircular electrodes (impedance electrodes), which are arranged on the surface of the front side of the tool 15 for example by vapor coating. Alternatively, the impedance electrodes can be arranged on the outerside of the probe body 11 at its end. The electrodes of the impedance sensor 33 are connected to the control device by means of electric connecting lines (not shown) along the probe body 11. Whenever a cell 21 migrates through the hollow channel 31 an impedance signal is generated, which announces the size and the electrical properties of the passing cell, by detuning the impedance between the impedance electrodes.

The carrying surface 16 carries an adhesion-enhancing coating. This connecting coating is preferably provided only on the carrying surface 16, whereas the surface of the remaining probe body 11 is preferably coated adhesion-minimising, to minimise migration and if necessary sliding between supplanted cells. The connecting coating comprises for example fibronectin. Silanising or coating with biological macromolecules (for example PolyHema, PTFE) can be provided for reduction of adhesion. Also the inner surface of the hollow channel can be coated adhesion-reducing in this way. At the leading edge (see part diagram B) the carrying surface 16 has a curvature. Due to corresponding lengthening of the leading edge the migration of cells is advantageously favoured.

The cross-sectional form of the capillary-shaped probe body is preferably round. Alternatively, a flattened elliptical form can be provided, which enables a predominant direction for the lateral movement in a direction of motion vertical to the longitudinal axis of the probe body 11.

FIG. 3 shows in the three part images A-C the individual phases of a cell transfer from a carrier 80 with a probe 10 to a target substrate 80' (in each case shown in part). Located on the carrier 80 is a cell culture 20 with several cells, of which one cell 21 is to be transferred to the target substrate 80'. On the carrier a fluid covering can be provided (see FIG. 2). The cell 21 is for example a stem cell found in the cell material 20.

The cell 21 first describes stochastic cell locomotion on the substrate 80, until it reaches the pick-up tool 15 and migrates to the latter by its own cell locomotion. This cell transfer can be caused by the adhesion-enhancing coating (see above) on the carrying surface 16 and/or an advance movement of the probe 10 opposite to the cell locomotion. Via the natural fluctuations of the adhesion contacts of the cell 21 these are gradually rearranged to the pick-up tool 15. As soon as the cell 21 is arranged fully on the probe (part image B), the probe 10 can then be retracted from the carrier 80 at increased speed. Further transport occurs dependent on the concrete application to the target substrate 80', where the cell 21 leaves the probe again due to its stochastic movement.

The movement of the cell 21 from the probe 10 to the target substrate 80' is advantageously already caused by the natural aggregation tendency of cells, in case there is already at least one cell present on the target substrate 80'. Alternatively, a molecular attractor, such as for example signal molecules, nutrients, hormones or chemotactically effective substances can be arranged on the target substrate 80' to promote the directional transfer.

Figure 4:
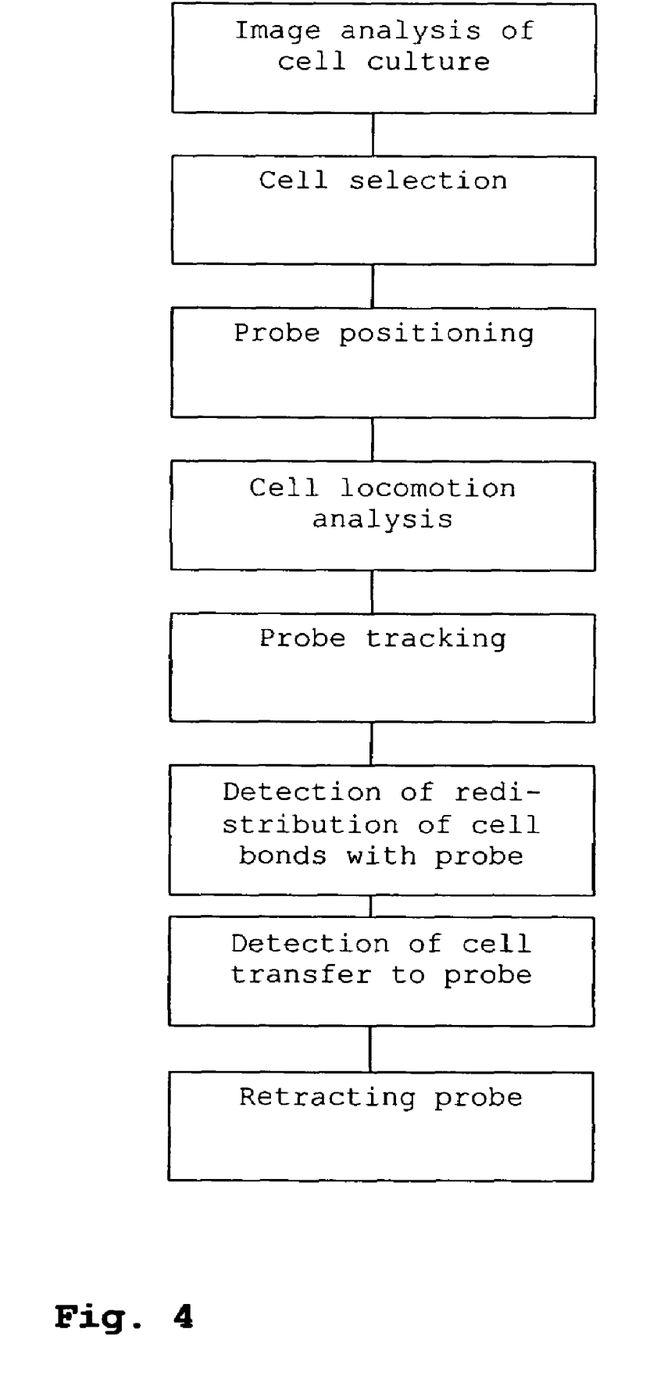
FIG. 4 is a flow diagram for illustrating an embodiment of an inventive method.

A method of operation of the cell transfer is given by way of example with further details in FIG. 4. Following image analysis on the cell culture 20 a desired cell 21 (e.g. a fibroblast or stem cell) is selected. Next come positioning of the probe 10 in the vicinity of the selected cell 21 and optical measuring and analysis of cell locomotion on the carrier 80, for finely adjusting and tracking the probe 10 relative to the cell locomotion. As soon as it has been confirmed that cell contacts were rearranged onto the probe, the direction of the probe tracking movement is adjusted such that transfer of the cell is promoted. After it has been confirmed that the cell has been fully transferred to the probe 10 a return traverse of the probe 10 from the carrier 80 takes place. The image analysis and detection steps take place using the detector device 70 (see FIG. 2).

Figure 5:
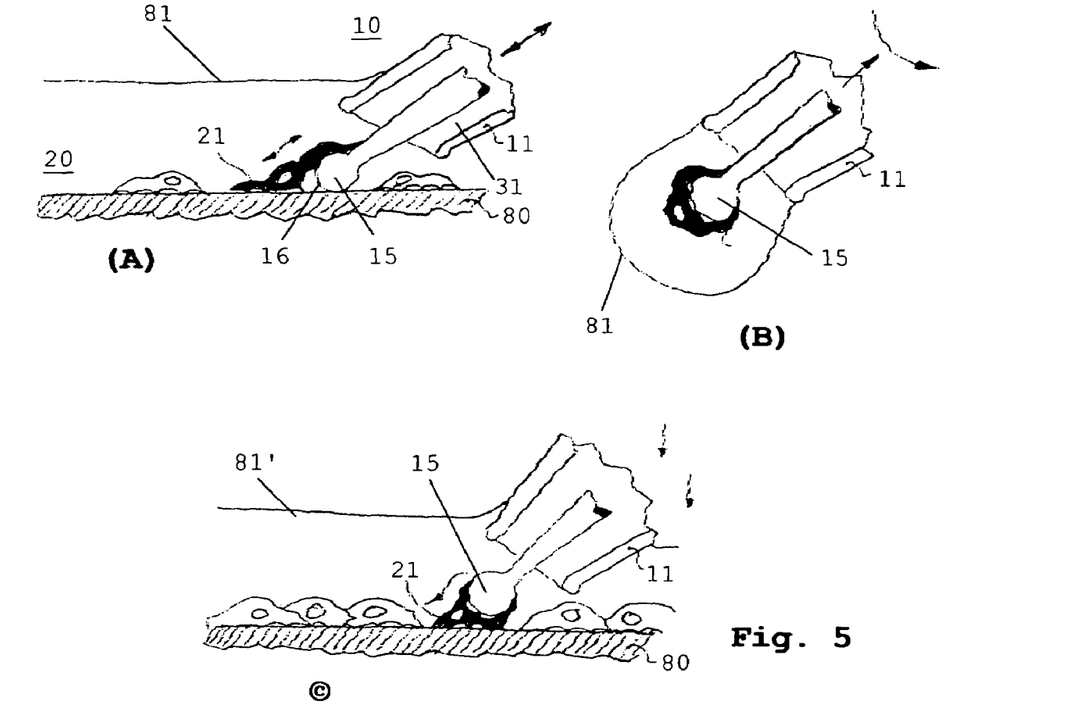
FIG. 5 shows the sequence of cell transfer steps according to a further embodiment of the inventive method.

FIG. 5 illustrates in part images A-C the cell transfer with a modified probe 10. Located in the hollow channel 31 of the capillary-like probe body 11 is the spherical pick-up tool 15, whereof the surface forms the carrying surface 16. The pick-up tool 15 has a diameter of for example 15 μm. The pick-up tool 15 can be shifted in the capillary-shaped probe body 11 with the drive device (see FIG. 2).

In accordance with part image A the probe 10 is dipped into the cultivation fluid 81 and moved to the substrate 80 with the cell culture 20, until the front end of the probe 10 is situated at a distance above the surface of the cell culture 20. Next, the pick-up tool 15 is moved out of the free end of the hollow channel 31, until it sits on the surface of the carrier 80. With this advance movement injury-free displacement of cell material takes place possibly situated along the path of the pick-up tool 15. Due to its natural intrinsic motion the cell 21 migrates to the carrying surface 16. When the cell 21 is located fully on the pick-up tool 15, the probe 10 can be lifted off the carrier 80. The return motion again occurs injury-free for the remaining cells of the cell culture 20. In the raised state the cultivation fluid 81 advantageously forms a fluid drop around the pick-up tool 15 (part image B). The cell is protected by this. During movement to the target substrate 80' the pick-up tool 15 can remain in the advanced position or be retracted. At the target substrate 80' the probe 10 is dipped in the suspension fluid 81' (part image C). Similarly to the abovedescribed procedure the cell 21 can be transferred to the target substrate 80' after sufficient approaching of the pick-up tool 15.

Similarly to the procedures shown in FIGS. 3 and 5 cells be arranged on or in tissue.

Figure 6:
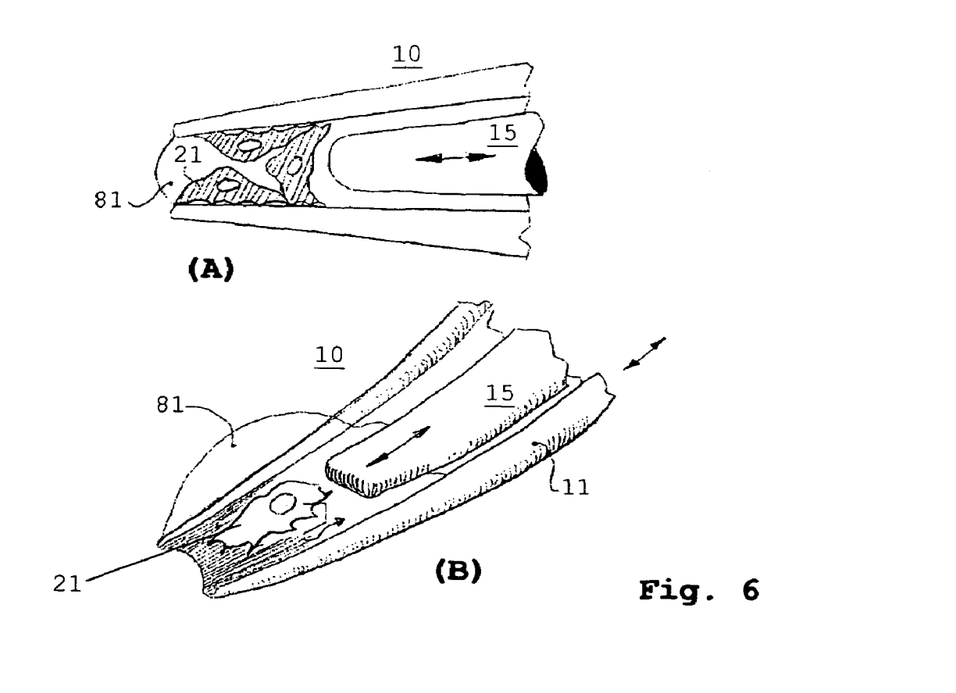
FIG. 6 shows further embodiments of inventive probes.

FIG. 6 illustrates cooperation of the probe body 11 with the pick-up tool 15 on an example of two modified embodiments of probes 10 used according to the present invention. In accordance with part image A the probe body 11 is a capillary, whereof the end is shown in section. The interior (hollow channel 31) of the capillary is filled with fluid. The pick-up tool 15 is a ram mobile in the capillary. In part image B the corresponding principle with an open slide is shown, which is formed for example similarly to FIG. 3 at the end of a capillary and in which a ram is likewise mobile. In both cases at least one cell 21 on the probe is covered with a fluid drop 81.

With the inventive cell transfer the ram 15 can be advanced and retracted as in FIG. 6 so as to pick up cells from a culture. Alternatively, the active cell migration provided according to the present invention can first take place into the hollow channel 31 and also onto the ram 15 in the latter. When stored on a target substrate the ram 15 can be used to pull out cells from the capillary 11 by means of injury-free displacement.

Figure 7:
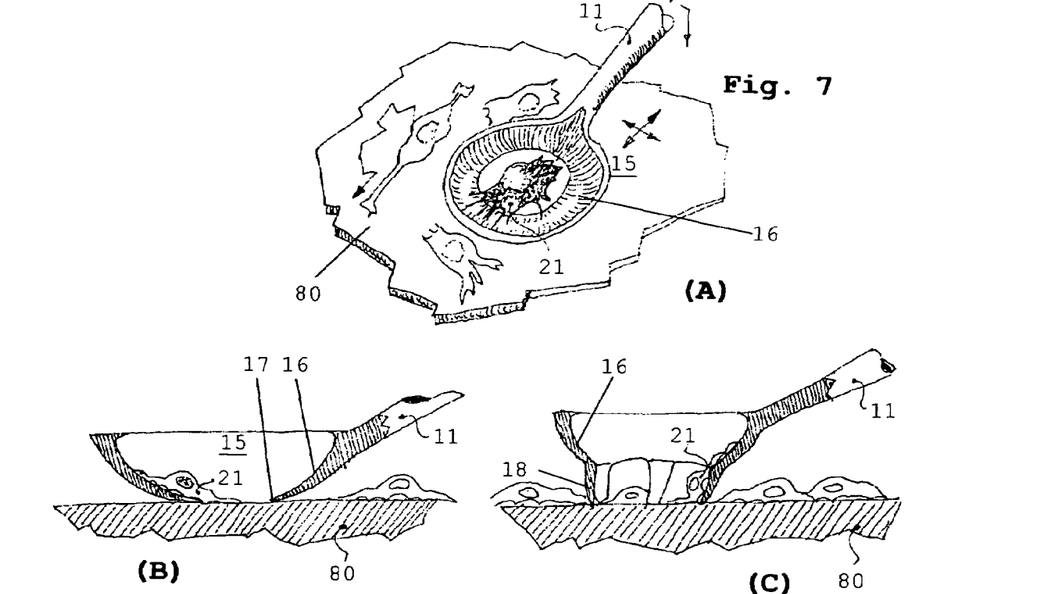
FIG. 7 shows the sequence of cell transfer steps using an inventive probe with an annular pick-up tool.

An important application of the invention comprises injury-free removal of cells from tissue (wound-free biopsy). A particular advantage of the invention consists in that even larger tools having dimensions, greater than the cells to be picked up, can be used for removing cell material e.g. for diagnostic purposes. FIG. 7 illustrates for example two variants of a pick-up tool with an annular carrying surface 16 used according to the present invention.

In accordance with part images A and B of FIG. 7 the pick-up tool 15 has a cross-section corresponding to the section of a spherical surface. The carrying surface 16 is formed on the inner side of the spherical surface. The inner edge 17 of the carrying surface 16 forms an opening, with which the probe 10 is set on the carrier 80 for the inventive cell transfer. In accordance with part image A the pick-up tool 15 is set down with the physiological reference velocity slowly over a desired cell 21. This will then move due to its natural cell locomotion from the carrier 80 to the carrying surface 16. As soon as this transfer is complete (part image B), the probe 10 be removed from the carrier 80.

Part image C of FIG. 7 illustrates the use of spacers 18, with which the pick-up tool 15 can be placed on the surface of the carrier 80. The spacers 18 facilitate setting the pick-up tool 15 and the selective migration of individual cells 21.

The pick-up tool 15 comprises one of the abovementioned materials, and it can have a diameter in the range of 10 μm to 10 mm and a height of 0.5 mm to 10 mm.

Figure 8:
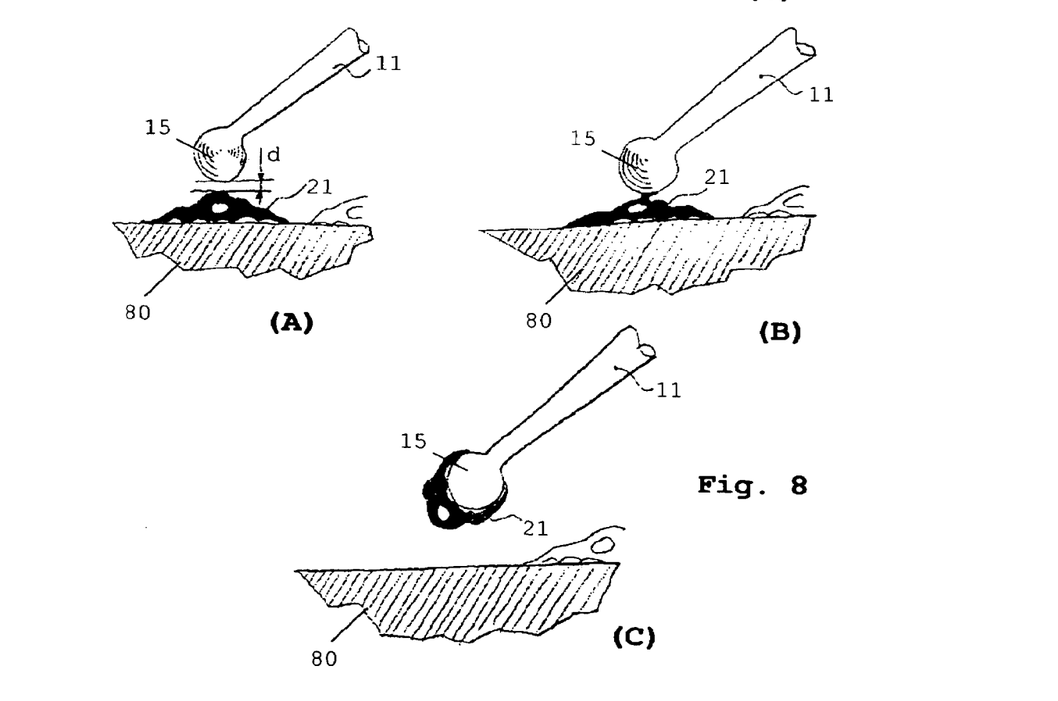
FIG. 8 shows the sequence of cell transfer steps according to a further embodiment of the inventive method.

FIG. 8 illustrates that the pick-up tool 15 for the cell transfer does not necessarily have to be placed on a cell culture. Rather it is possible, according to part image A, to set the transfer arrangement first with a distance d between the pick-up tool 15 and the cell 21. The distance d can be selected for example in the range of a few hundred nm to a few micrometers (e.g. 5 μm). Then short-time contact (duration 5 s to a few minutes) of the carrying surface 16 with the cell 21 takes place according to part image B, to start the cell transfer. The inventors have found that adherent sticking at each position on the cell surface is possible and that the cell transfer can take place over the distance d. In the illustrated example the pick-up tool 15 is preferably formed from a transparent material so that the procedure of adhesion and cell transfer can be observed optically, e.g. with a microscope. For distortion-free observation the pick-up tool 15 has a planar surface, formed for example by a flat plate.

Figure 9:
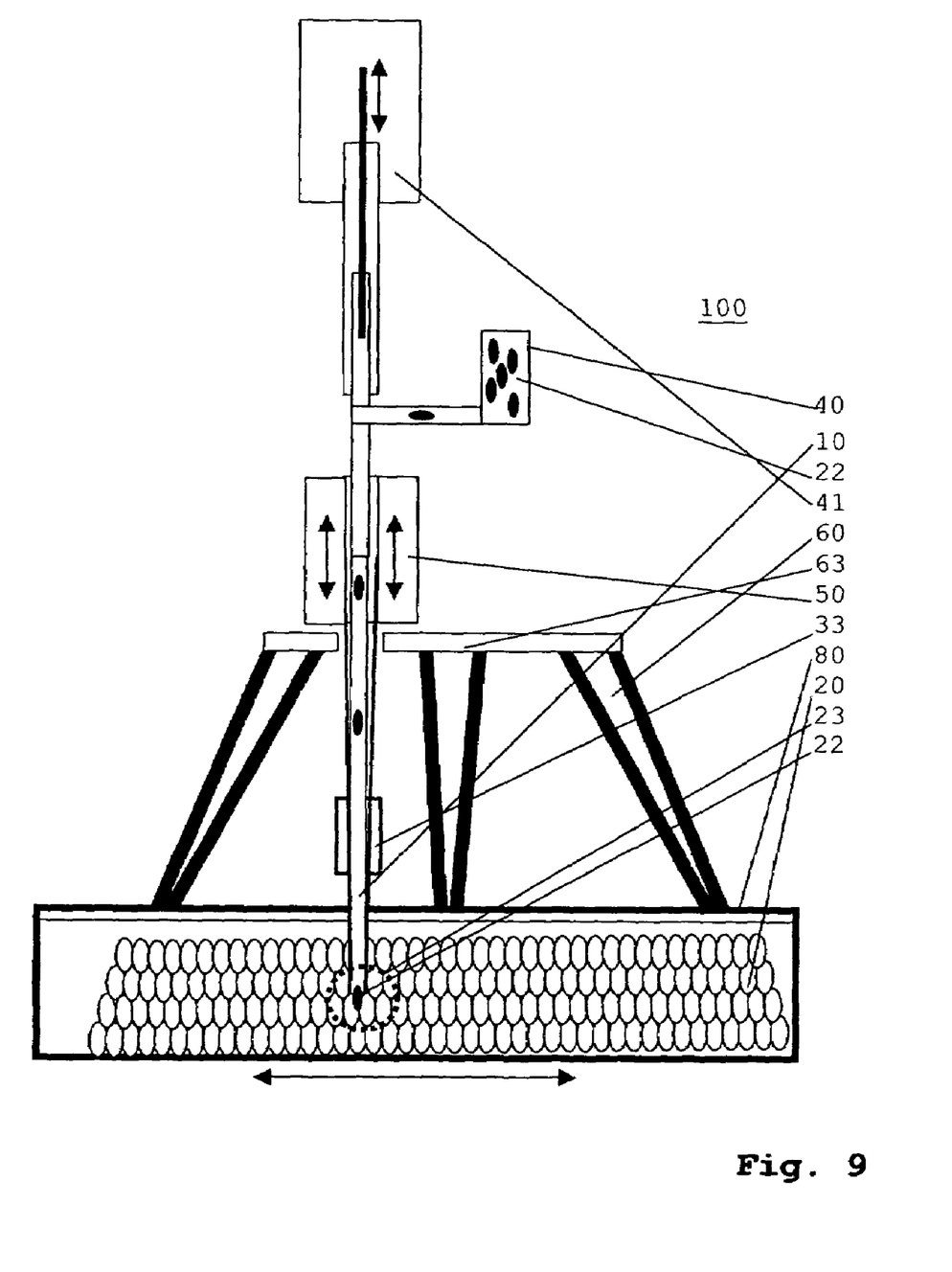
FIG. 9 is an illustration of further details of an embodiment of an inventive cell manipulator.

In FIG. 9 further details of the cell manipulator 100 are shown in an example of an in-vitro system for biotechnology (tissue engineering). The goal is to inject one or more cells 22 from a cell reservoir 40 into a cell tissue bond 20 using a microcapillary (probe 10). The probe 10 is connected via a duct system to the cell reservoir 40. Thereby, the probe 10 is connected with a Hamilton syringe (transport system 41 for the cell suspension 22), which is actuated by a processor or a computer (not shown). The entire system is located on a work platform 63, which cannot be moved relative to the tissue bond 20, since it is connected via the positioning device 60 solidly to the carrier (culture dish 80).

The basic adjusting of the work platform 63 occurs with the positioning device 60. The advance system or drive device 50 for the probe 10 is a piezo tube, which can expand or contract in the given manner and in doing so introduce the probe 10 into the tissue bond 20 or respectively withdraw it. A target cell area 23 (spot-welded ring) is illustrated, into which a cell 22 is just inserted. Situated on the shaft of the capillary probe 10 is a single cell detector system 33, with which the number of injected cells can be determined (here shown as an optical system).

The cell manipulator 100 corresponding to FIG. 9 is actuated as follows. In a first step the positioning device 60 is connected solidly with the target tissue 20. This occurs by fixing the positioning unit to the culture dish 80 or on the surface of an organism or respectively a suitable part of the bone structure. In a second step the micro-injection tool 10 is fastened to the work platform 61 and roughly preadjusted, so that it is localised with its tip shortly before the target tissue or cell system 20. In the next step the capillary of the probe 10 is filled with the nutritional solution, a physiological solution or another suitable fluid and guided to the target tissue until they make contact. After this the programmed advance occurs of the micro-injection tool corresponding to the speed of for example less than 1 µm/h to a few 100 µm/h, until the target area 23 is reached. Either at this time or earlier the cells to be injected are rinsed from the reservoir in the micro-injection tool and detected by the detector as they pass the recessed part, then counted and if necessary characterised. By moving the injection tool in all three spatial directions at the above-mentioned low velocity, the system can be guided into a new target area, so that in a previously estimable manner cells are positioned three-dimensionally in the tissue. Transfer of at least one cell takes place at the desired site in the target tissue by its natural intrinsic motion, and possibly is supported by a pressure exerted by the suspension fluid. On completion of injection the micro-injection tool is again removed from the target tissue. The low velocity, also designated as "physiological velocity", allows the cells of the tissues at the tip of the injection tool to detach the cell adhesion contacts, resulting in an ordered displacement of the cells, without their being injured.

The features of the invention disclosed in the above description, the claims and the diagrams can be significant both individually or also in combination for carrying out the invention in its different configurations.

The invention claimed is:

1. A cell transfer method, comprising the steps of:
   positioning of a probe and a carrier relative to one another in a transfer arrangement; and
   transfer of at least one biological cell between the carrier and the probe, wherein the cell describes a natural cell locomotion and the transfer of the cell takes place due to the natural cell locomotion.

2. The method as claimed in claim 1, wherein the cell is transferred from the carrier to the probe.

3. The method as claimed in claim 2, wherein the cell is transferred from a composite with cell material, which is arranged on the carrier, to the probe.

4. The method as claimed in claim 2, wherein properties of the cell are detected with the probe.

5. The method as claimed in claim 2, wherein the probe with the cell is removed from the carrier.

6. The method as claimed in claim 1, wherein the cell is transferred from the probe to the carrier.

7. The method as claimed in claim 6, wherein the cell is conveyed by the probe into cell material arranged on the carrier.

8. The method as claimed in claim 1, wherein the positioning of the probe and of the carrier into the transfer arrangement takes place such that the probe contacts the carrier.

9. The method as claimed in claim 1, wherein the positioning of the probe and of the carrier into the transfer arrangement takes place such that the probe is at a distance from the carrier less than or equal to an extension of at least one cell above the carrier.

10. The method as claimed in claim 1, wherein the transfer arrangement is modified by the probe and the carrier being moved relative to one another.

11. The method as claimed in claim 10, wherein the positioning of the probe and of the carrier into the transfer arrangement takes place such that the probe is at a distance from the cell material arranged on the carrier, and a temporary contact of the cell is made with the carrier or the probe.

12. The method as claimed in claim 10, wherein the probe and the carrier are moved during cell transfer relative to one another with a predetermined advance direction equal to a preferred direction of feed of the probe.

13. The method as claimed in claim 12, wherein the probe has a longitudinally extending form with a longitudinal direction, which forms the preferred direction of feed.

14. The method as claimed in claim 11, wherein the probe and the carrier are moved relative to one another for forming the temporary contact or for the cell transfer with a velocity of advance which is less than or equal to a physiological reference velocity of the cell locomotion.

15. The method as claimed in claim 14, wherein the probe and the carrier are moved relative to one another with a velocity of advance from 0.1 µm/h to 1 mm/h.

16. The method as claimed in claim 1, further comprising:
    determining the position of the cell to be transferred on the carrier or the probe prior to cell transfer; and
    positioning or moving the probe and the carrier relative to one another dependent on a result of the determining step.

17. The method as claimed in claim 16, further comprising:
    movement detection of the cell to be transferred on the carrier or the probe prior to or during the cell transfer; and
    positioning or moving the probe and the carrier relative to one another dependent on the movement detection.

18. The method as claimed in claim 1, wherein the transfer step comprises simultaneously or successively transferring a plurality of cells between the carrier and the probe.

19. The method as claimed in claim 1, wherein cell transfer is carried out in vitro.

\* \* \* \* \*